United States Patent
Borzello et al.

(10) Patent No.: US 8,635,233 B2
(45) Date of Patent: Jan. 21, 2014

(54) TECHNIQUES TO AUTOMATICALLY BUILD A LANGUAGE DEPENDENCY GRAPH FOR LOCALIZABLE RESOURCES

(75) Inventors: Eric Borzello, Redmond, WA (US); Zhigiang Feng, Snoqualmie, WA (US); Huy Nguyen, Bothell, WA (US)

(73) Assignee: Microsoft Corporation, Redmond, WA (US)

( * ) Notice: Subject to any disclaimer, the term of this patent is extended or adjusted under 35 U.S.C. 154(b) by 102 days.

(21) Appl. No.: 13/169,936

(22) Filed: Jun. 27, 2011

(65) Prior Publication Data

US 2012/0330985 A1      Dec. 27, 2012

(51) Int. Cl.
G06F 7/00      (2006.01)
G06F 17/30     (2006.01)
G06F 19/26     (2011.01)
G06F 19/00     (2011.01)

(52) U.S. Cl.
CPC .............. G06F 19/26 (2013.01); G06F 19/708 (2013.01)
USPC ............ 707/756; 707/797; 707/798; 707/811

(58) Field of Classification Search
CPC .............................. G06F 19/26; G06F 19/708
USPC ........................... 707/726, 797, 798, 811, 756
See application file for complete search history.

(56) References Cited

U.S. PATENT DOCUMENTS

| | | | |
|---|---|---|---|
| 6,090,156 A * | 7/2000 | MacLeod | 717/157 |
| 6,865,716 B1 | 3/2005 | Thurston | |
| 7,669,124 B2 | 2/2010 | Ye et al. | |
| 7,698,124 B2 * | 4/2010 | Menezes et al. | 704/3 |
| 7,698,126 B2 | 4/2010 | Kohlmeier et al. | |
| 8,126,698 B2 * | 2/2012 | Washizawa et al. | 704/2 |
| 8,209,164 B2 * | 6/2012 | Etzioni et al. | 704/2 |
| 2005/0065771 A1 * | 3/2005 | Chen et al. | 704/2 |
| 2006/0095248 A1 * | 5/2006 | Menezes et al. | 704/3 |
| 2008/0103757 A1 * | 5/2008 | Washizawa et al. | 704/2 |
| 2009/0132233 A1 * | 5/2009 | Etzioni et al. | 704/3 |
| 2010/0121630 A1 * | 5/2010 | Mende et al. | 704/7 |

OTHER PUBLICATIONS

Caron, et al., "DotNetNuke Localization", Retrieved at <<http://www.dotnetnuke.com/LinkClick.aspx?fileticket=sMOUQP7nHr8%3D&tabid=478&mid=857>>, Jun. 20, 2006, pp. 26.
"Localizing Silverlight-based Applications", Retrieved at <<http://msdn.microsoft.com/en-us/library/cc838238(v=vs.95).aspx>>, Retrieved Date: Mar. 22, 2011, pp. 9.
"windows-presentation-foundation.com", Retrieved at <<http://windows-presentation-foundation.com/WPF_Global_Applications.aspx>>, Retrieved Date: Mar. 23, 2011, pp. 5.
Abel, Todd, "Enterprise Localization Toolkit", Retrieved at <<http://msdn.microsoft.com/en-us/library/aa479334.aspx>>, May 2002, pp. 21.

\* cited by examiner

*Primary Examiner* — Phong Nguyen (57) ABSTRACT

Techniques to automatically build a language dependency graph for localizable resources are described. A technique may include storing resources from a file in a translation database with data that indicates the language that the resource is in, the entity that created that version of the resource, and a dependency, if any, on a different language version of the resource. Subsequent translations of a resource may also be stored in the translation database in a manner that groups the translated version(s) of a resource to the original resource, and also stores the language of the resource, the entity that translated it, and the dependency to the language from which the resource was translated. A language dependency graph may be generated from the translation database for a file, where the graph reflects the languages of translation and dependency relationships among the translations. Other embodiments are described and claimed.

17 Claims, 8 Drawing Sheets

```
STORE A RESOURCE FROM A FILE IN A DATABASE ENTRY,
INCLUDING DATA INDICATING AN ENTITY OF ORIGIN AND
AN ORIGINAL LANGUAGE
402
```

```
TRANSLATE A RESOURCE FROM AN ORIGINAL LANGUAGE
TO A SECOND LANGUAGE
404
```

```
ADD, TO THE DATABASE ENTRY FOR THE RESOURCE, THE
TRANSLATED RESOURCE AND DATA INDICATING THE
TRANSLATING ENTITY AND THE SECOND LANGUAGE
406
```

```
GENERATE A LANGUAGE DEPENDENCY GRAPH FOR THE
FILE
408
```

```
STORE THE LANGUAGE DEPENDENCY GRAPH FOR THE
FILE IN A DATABASE ENTRY ASSOCIATED WITH THE FILE
410
```

- IDENTIFY AN ERROR IN A RESOURCE IN A FIRST LANGUAGE CORRESPONDING TO A FIRST NODE
  602

- EXAMINE THE LANGUAGE DEPENDENCY GRAPH OF THE FILE UPSTREAM FROM THE FIRST NODE TO IDENTIFY NODES THAT THE FIRST NODE DEPENDS ON
  604

- CHECK THE RESOURCE IN THE LANGUAGE CORRESPONDING TO EACH IDENTIFIED NODE FOR AN ERROR AND CORRECT THE ERROR AT THE HIGHEST UPSTREAM NODE WHERE THE ERROR OCCURS
  606

- CORRECT THE ERROR IN THE RESOURCE IN EACH OF THE LANGUAGES CORRESPONDING TO THE NODES DOWNSTREAM FROM THE HIGHEST UPSTREAM NODE
  608

- UPDATE THE TRANSLATION DATABASE WITH THE CORRECTED RESOURCES
  610

TECHNIQUES TO AUTOMATICALLY BUILD A LANGUAGE DEPENDENCY GRAPH FOR LOCALIZABLE RESOURCES

BACKGROUND

Some computer software applications can be provided in different languages for different consumer markets, a process referred to as localization. An application may use one or more resources, such as text strings, and the resources may be grouped, for example, in files, such as library files, .dll files, and so forth. Typically, an application program and its resources are written in one language, and then translated into other languages. In some cases, the translations may not always start from the original language, for example, when translating from one language into a dialect or localized subset of the language, such as Spanish to Catalan, for example. Further, translations to different languages may be performed by different entities. When an error is found in a resource, or its translated forms, or when an update is needed, locating the source of the error in a stream of translations may be challenging. Further, it may be difficult to ensure that an update is properly localized. It is with respect to these and other considerations that the present improvements have been needed.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Various embodiments are generally directed to techniques to automatically build a language dependency graph for localizable resources. Some embodiments are particularly directed to techniques to build a language dependency graph for efficient loading of the localized resources. In one embodiment, for example, a technique may comprise storing resources in a translation database with data that indicates the language that the resource is in, the entity that created that version of the resource, and a dependency, if any, on a different language version of the resource. Subsequent translations of a resource may also be stored in the translation database in a manner that groups the translated version(s) of a resource to the original resource. The translations may also be stored with the language of the resource, the entity that translated it, and the dependency to the language from which the resource was translated. A language dependency graph may be generated from the translation database for a group of related resources, where the graph reflects the languages of translation and dependency relationships among the translations. Other embodiments are described and claimed.

These and other features and advantages will be apparent from a reading of the following detailed description and a review of the associated drawings. It is to be understood that both the foregoing general description and the following detailed description are explanatory only and are not restrictive of aspects as claimed.

DETAILED DESCRIPTION

Various embodiments are directed to techniques and systems to automatically generate a language dependency graph for localizable resources. Applications that operate on computing platforms often make use of a number of resources, such as libraries or .dll files. The resources are usually initially written in one language. In order to make the application appealing to users in markets where other languages are spoken, applications can be "localized" by translating the human-language portions of the application into the local language. For example, menu selection resources such as "Load" and "Save" that appear in an interface may be translated from English into French, Chinese, Hindi, and so forth.

Conventionally, when a translated resource was loaded at run-time by a localization application, a relationship between the translated versions would have to be determined and loaded for each resource separately. A call to a resource would, conventionally, have to include the source and target languages, which the code developer might not know. For each resource, the relationship between target and source language would have to be determined, resulting in a computational expensive incremental loading.

The embodiments described herein may store resources, and translated versions of the resources, in a translation database that keeps track of the languages of translation, the entities that performed the translations, and dependency relationships among the translations. This information may be used to generate one language dependency graph for a group of resources. The language dependency graph may represent all of the languages in which the group of resources has been localized, as well as the relationships of the translations, e.g. source language and target language. Being able to load one language dependency graph at run-time that can be used for all of the resources in the group may provide substantial efficiencies for the localization application. The language dependency graph may also simplify and improve the process of tracing an error in a translated resource to its source, as well as the propagation of modifications and updates to all resources in a language dependent on the language of a modified resource.

Figure 1:
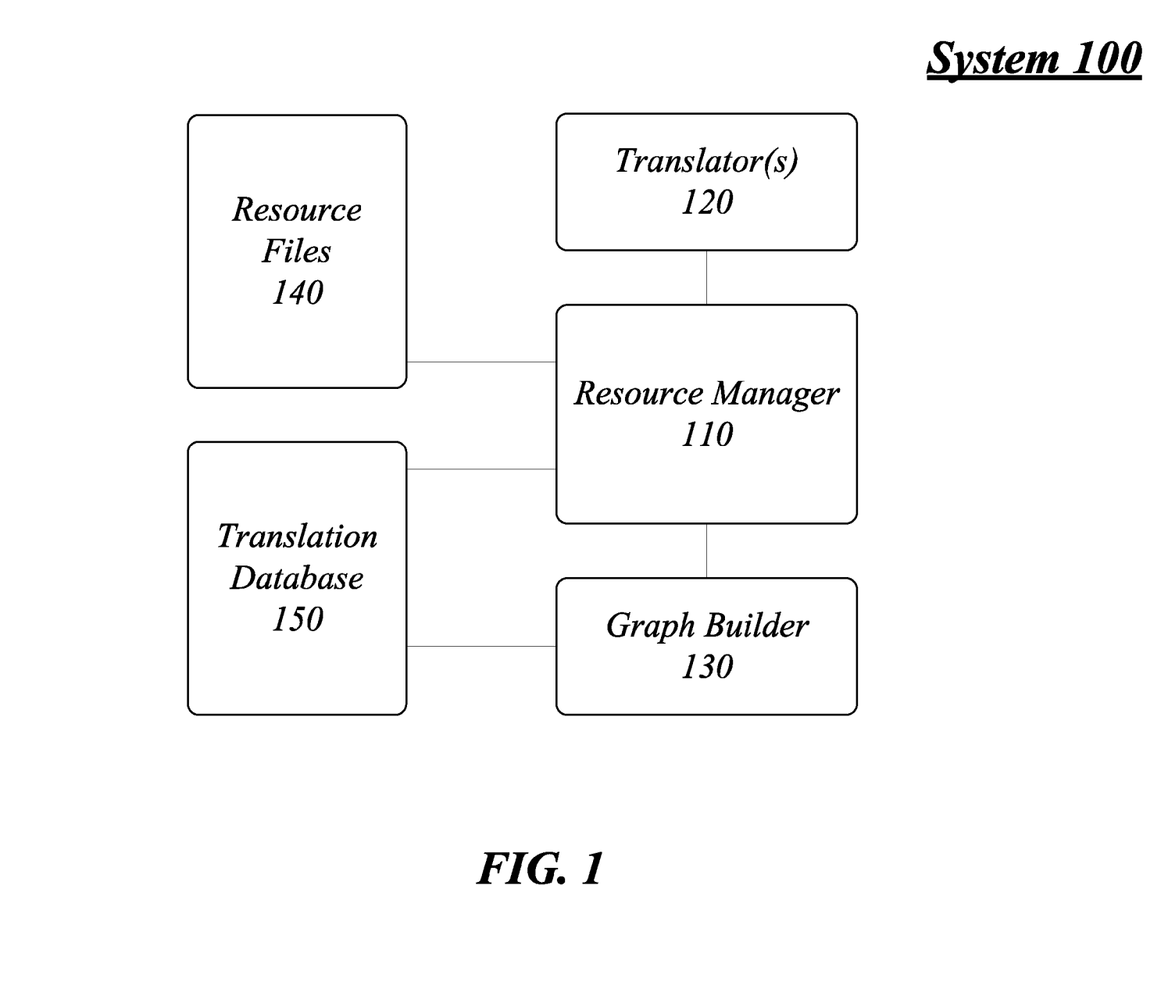
FIG. 1 illustrates an embodiment of a system for automatically building a language dependency graph.

FIG. 1 illustrates a block diagram for a system 100 for automatically building a language dependency graph for localizable resources. In one embodiment, for example, the system 100 may comprise a computer-implemented system 100 having multiple components, for example, a resource manager 110, a translator 120 and a graph builder 130. As used herein the terms "system" and "component" are intended to refer to a computer-related entity, comprising either hardware, a combination of hardware and software, software, or software in execution. For example, a component can be implemented as a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers as desired for a given implementation. The embodiments are not limited in this context.

In the illustrated embodiment shown in FIG. 1, the system 100 may be implemented as part of an electronic device. Examples of an electronic device may include without limitation a mobile device, a personal digital assistant, a mobile computing device, a smart phone, a cellular telephone, a handset, a one-way pager, a two-way pager, a messaging device, a computer, a personal computer (PC), a desktop computer, a laptop computer, a notebook computer, a handheld computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, television, digital television, set top box, wireless access point, base station, subscriber station, mobile subscriber center, radio network controller, router, hub, gateway, bridge, switch, machine, or combination thereof. Although the system 100 as shown in FIG. 1 has a limited number of elements in a certain topology, it may be appreciated that the system 100 may include more or less elements in alternate topologies as desired for a given implementation.

The components 110, 120, and 130 may be communicatively coupled via various types of communications media. The components 110, 120, and 130 may coordinate operations between each other. The coordination may involve the uni-directional or bi-directional exchange of information. For instance, the components 110, 120 and 130 may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

In various embodiments, the system 100 may comprise resource manager 110. Resource manager 110 may manage the translation of resources, and storing the resources and their translations in such as way as to permit the building of a language dependency graph. Resource manager 110 and its functions are described further below.

In various embodiments, the system 100 may comprise one or more translators 120. Translators 120 may include entities that translate resources from one language into at least one other language. A translator 120 may include, for example, a person, a business entity that performs translations as a service, or a computer application that translates. A translator 120 may be part of the same entity that generates the resources, or may be a third-party entity to which the resource-generating entity sends resources for translating, and receives the translated resources. System 100 may maintain unique identification for each separate translator 120 to facilitate error tracking and update functions.

In various embodiments, system 100 may comprise graph builder 130. Graph builder 130 may generate and update a language dependency graph for a group of resources, for example, a file of resources. A language dependency graph may include nodes for each language in which a resource exists, and connections between the nodes that reflect the dependency of a translation. The dependency refers to which language a resource was translated from (source), and which language a resource was translated to (target). Language dependency graphs are discussed further below with respect to FIG. 3.

In various embodiments, the system 100 may comprise resource files 140. Resource files 140 may include groups of resources that may be related. As described herein, the term "file" referring to resource files 140 is not limited to a file in a hierarchical storage structure, but may refer to any grouping of resources. The groups may be files, or other logical groupings, such as database tables and the like. An example of a resource file 140 may include a .dll file, a header file, a library file, a help file, or other file or group of resources used by an application in operation. Resource files 140 may be provided with an application by the application provider when the application is installed or run on a computing device. In an embodiment, resource files 140 may include resources such as strings that may be used in the application's user interface, for example, as menu listings, button text, messages in a dialog box, error messages, help instructions and so forth. Resources may also include other forms of data that include language that would need to be translated in order to localize the application using the resource.

In various embodiments, the system 100 may comprise translation database 150. Translation database 150 may be generated and maintained by resource manager 110. Translation database 150 may include data about the resources in resource files 140, including, for example, the resource in its original language and the resource in each of the languages into which it has been translated. The data about the resources may also include an indication of what language the resource is in, and an indication of which translator 120 performed the translation. Translation database 150 may further record the relationships between the different translations of a resource. In an embodiment, the data for all of the resources in one resource file 140 may be included in one logical database grouping, such as one table. In an embodiment, translation database 150 also includes a language dependency graph for each resource file 140 in the database. An example of a translation database is provided and discussed below with respect to FIG. 2.

Figure 2:
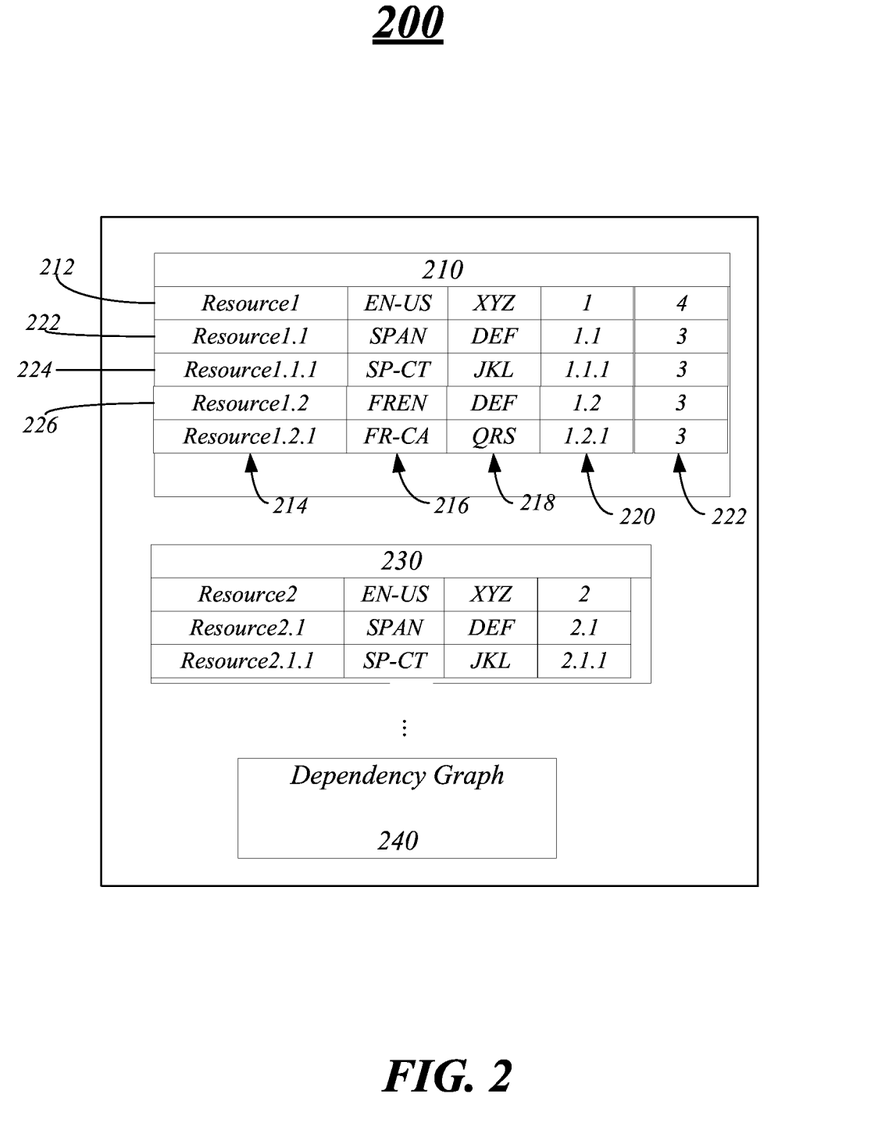
FIG. 2 illustrates an embodiment of a translation database entry.

FIG. 2 illustrates an example of a section of a translation database 200 corresponding to one resource file 140. Translation database 200 may be a representative embodiment of a section of translation database 150. Other embodiments of a translation database are possible.

In various embodiments, the translation database 200 may comprise a data entry for each resource in a resource file. For example, data entry 210 may be associated with resource1, and data entry 230 may be associated with resource2.

Each data entry may have one or more fields and sub-fields to store translated resources and data about the translations. Each field (e.g., field 212) may correspond to one version of the resource in one language. For example, field 212 may include a sub-field 214 to store the resource, e.g. a string. Field 212 may also include a sub-field 216 to store an indicator as to what language the resource is in. The indicator may comprise some unique identifier, for example, a letter code, a number code, a symbol code, and so forth. The indicator may be a pointer to another table that indicates the language. The embodiments are not limited to these examples. Field 212 may further include a sub-field 218 to store an indicator as to what entity performed the translation. For the original resource, sub-field 218 may indicate the entity of origin. The indicator may comprise some unique identifier for the translating entity, as described above.

In an embodiment, field 212 may further include a sub-field 220 that indicates the dependencies of the translations. For example, sub-field 220 may include a numeric convention to indicate dependency. For example, the sub-field 220 for the original resource in field 212 may be assigned the value "1". The first resource (in field 222, in Spanish) translated from that original resource may be assigned the value "1.1", where the left "1" indicates the original resource, and the right "1" indicates the first translated resource. The first resource translated from the Spanish resource may be assigned the value "1.1.1", where the left-most "1" indicates the original resource, the middle "1" indicates the Spanish resource, and the right-most "1" indicates this is the first translation from "1.1"—the Spanish resource. The resource in field 226 is translated from the original resource into French. The value in sub-field 220 for field 226 may be assigned "1.2", where the "1" indicates the original resource, and the "2" indicates the second translation from the original.

In another embodiment, sub-field 220 may include a pointer to the resource field for the resource that was the origin of the translation. For example, the resource in field 224, in Catalan, may have been translated from the Spanish version of the resource in field 222, and sub-field 220 for field 224 may point to field 222. Other implementations are possible where the path of translations for each language version of a resource may be traced back to the original resource.

Data entry 230 may be structured as for data entry 210, and contain data relating to resource2 and its translations. In an embodiment where a numbering scheme is used to indicate dependencies, the original number may be a number unique to resource2, e.g. "2".

In an embodiment, a data field may include a sub-field 222 that indicates a revision number for the resource. Resource manager 110 may update sub-field 222, e.g. by incrementing the revision number, each time the resource in the field is modified. For example, the English resource in field 212 has been revised three times (if the original version has revision number 1), while the other language version resources that depend from the English resource have only been revised twice. In an embodiment, a localizing application may check the translation database to determine whether an upstream resource has been modified, e.g. when the revision numbers don't match. When the revision numbers don't match, the localizing application may proceed to update the downstream resource or flag the resource as needing an update.

The section of a translation database 200 corresponding to one resource file 140 may further comprise a dependency graph 240 constructed from data about all of the resources in the resource file. Dependency graph 240 may include information about all of the languages into which the resources in the file were translated, and the dependencies of each translation to other languages and the original resource. Dependency graph 240 may be constructed, for example, using the data in sub-fields 216 and 220. Dependency graph 240 may include, for example, a node for each language that occurs in the section of translation database 200, and a relationship between each node, if any.

Translation database 200 may include sections for each separate group of related resources, e.g. for each resource file, and may store one language dependency graph 240 per group or file.

Figure 3:
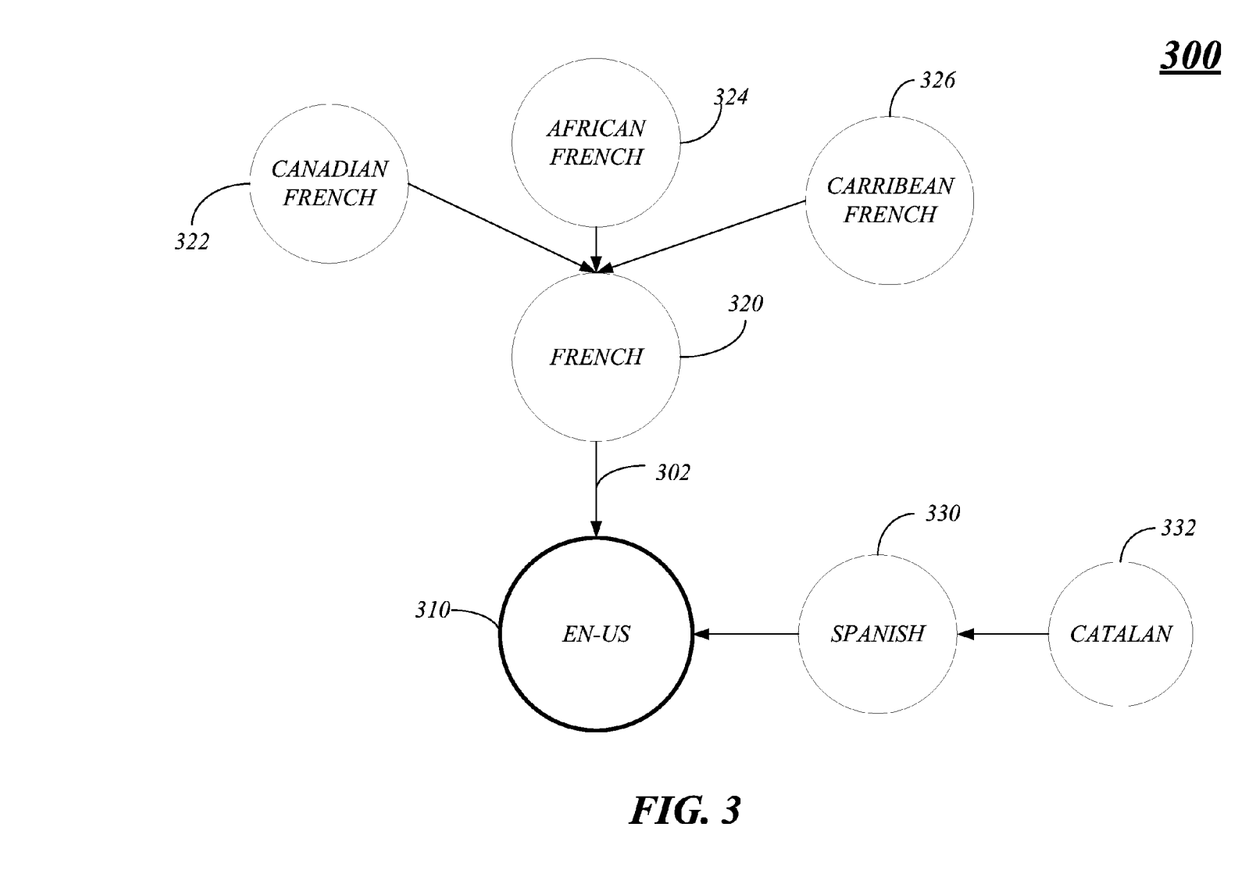
FIG. 3 illustrates an embodiment of a language dependency graph.

FIG. 3 illustrates a graphical representation of a language dependency graph 300. Language dependency graph 300 may be constructed from data in a section of a translation database corresponding to a file having resources translated into six languages from an original language.

Language dependency graph 300 shows, for example, an original language node 310 for American English. The graph further shows that, from English, resources were translated into French (node 320) and Spanish (node 330). The dependency relationship between nodes, e.g. node 320 and node 310, may be shown with a line or an arrow (e.g., arrow 302) that indicates the direction of dependency for the translation. For example, the French translation was done from the English translation, so the French translation depends from the English translation.

The graph 300 further shows that additional translations were performed. French resources (node 320) were translated from French into three different variants of French: Canadian French (node 332), African French (node 324), and Caribbean French (node 332). Each of nodes 322, 324 and 326 depends from node 320, and are independent of each other. Spanish resources (node 330) were translated into Catalan (node 332).

In the event that an error is discovered, for example, in a resource in Canadian French, the language dependency graph 300 may be used to determine where to search for the origin of the error. The error may be, for example, in node 322, in node 320, or in node 310. If, for example, a resource in French node 320 were mis-translated into Canadian French node 322, then the resource in French could be examined first to determine if the French resource was correct. If so, then only the Canadian French resource would need to be corrected. If, however, the error occurred further "upstream" in the translation process, e.g. in the French translation or in the original English, then the process of searching for the error may proceed along the dependency relationship lines.

Once the error is located, for example, in a French resource (node 320), then that resource may be corrected, and the correction may need to be applied to all downstream nodes, e.g. to resources for nodes 322, 324 and 326. The translation database 150 may be used to identify the translators 120, who may be contacted to effect the correction. Similarly, when a resource is modified or updated in the original version, the language dependency graph may be used to identify in what languages the resource will need to be updated as well.

While it is possible for each individual resource to have its own language dependency graph, in practice, most resources in a group, e.g. a file, have the same language dependency graph. By generating and storing a language dependency graph for a group of resources, rather than for each individual resource, efficiencies in loading a resource may be obtained, as only one language dependency graph needs to be loaded. In the event that a resource has a different language dependency graph, its individual graph may be loaded as needed.

Being able to determine all of the languages and translators 120 in a dependency relationship may similarly improve translation efficiency. All translators in a stream may be notified that translation or correction work is coming, for example, for an update or when an error is detected, and the translators may be able to allocate translation resources appropriately ahead of time to speed up the process.

In most cases, the secondary translation language may be a derivative of the first translation language, meaning that the two languages are substantially related, e.g. Spanish to Catalan. Such a relationship is not required however, and it is possible to translate, for example, English to Dutch to Japanese. In such a case, the language dependency graph would contain nodes for English, Dutch and Japanese, where Dutch depended on English, and Japanese depended on Dutch. The various embodiments allow these paths of translations without the end-user having to be aware of them, while still allowing a single language dependency graph to be generated for the file having resources translated along such a path.

Operations for the above-described embodiments may be further described with reference to one or more logic flows. It may be appreciated that the representative logic flows do not necessarily have to be executed in the order presented, or in any particular order, unless otherwise indicated. Moreover, various activities described with respect to the logic flows can be executed in serial or parallel fashion. The logic flows may be implemented using one or more hardware elements and/or software elements of the described embodiments or alternative elements as desired for a given set of design and performance constraints. For example, the logic flows may be implemented as logic (e.g., computer program instructions) for execution by a logic device (e.g., a general-purpose or specific-purpose computer).

Figure 4:
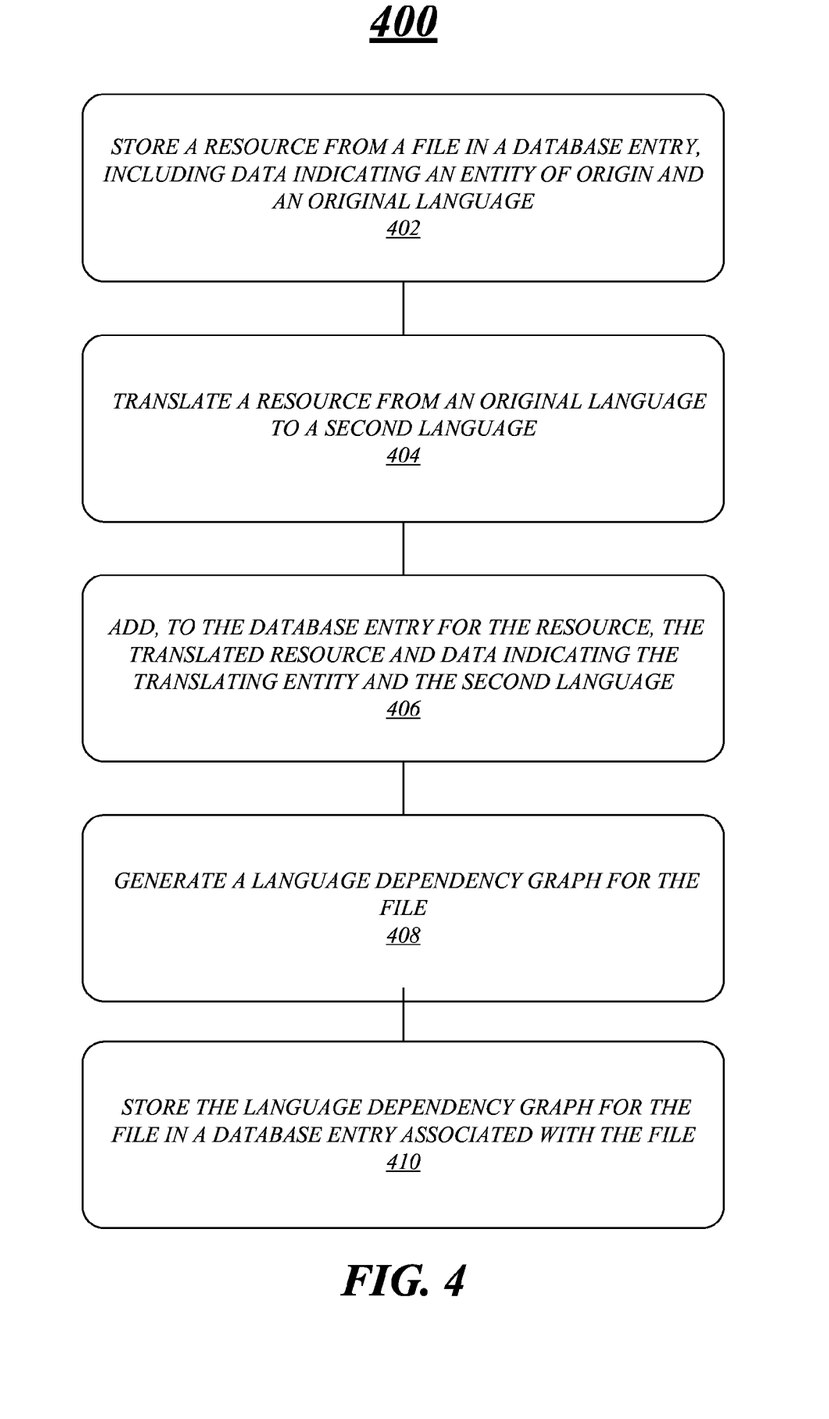
FIG. 4 illustrates an embodiment of a logic flow for building a dependency graph.

FIG. 4 illustrates one embodiment of a logic flow 400. The logic flow 400 may be representative of some or all of the operations executed by one or more embodiments described herein.

In the illustrated embodiment shown in FIG. 4, the logic flow 400 may store a resource from a file in a database entry at block 402. For example, resource manager 110 may create an entry in translation database 150 for each resource in a resource file 140. Each entry may include the resource or a link to the resource. Each entry may also include data that indicates the entity of origin and the original language.

The logic flow 400 may translate a resource from an original language to a second language at block 404. For example, the entity of origin may use translators 120 to translate the resources. Translators 120 may be internal translating resources, such as people or computer applications. Translators 120 may be external translating entities that provide a translation service to the entity of origin.

The logic flow 400 may add a translated resource to the database at block 406. For example, resource manager 110 may receive the translated resource from a translator 120, and may add the translated resource to the translation database 150 in a field in the entry for the original resource. The added field may include the translated resource, or a link to the translated resource. The added field may further include data indicating the translating entity and the second language. The data may also include relationship information indicating a dependency to the original language.

The logic flow 400 may generate a language dependency graph for a resource file at block 408. For example, graph builder 130 may generate a language dependency graph by generating a node for the original language and a node for the second language, and a relationship between the nodes indicating that the second language node depends from the original language node.

The logic flow 400 may store the language dependency graph for the resource file in a database entry at block 410. For example, resource manager 110 may store the language dependency graph in translation database 150 such that the graph is associated with the resource file from which it was generated.

When a resource file 140 contains more than one resource, blocks 402, 404 and 406 may be repeated for all of the resources in the resource file. Once all of the resources are translated, blocks 408 and 410 may occur. Logic flow 400 may be repeated in its entirety for additional translations, either from the original language or from a translated resource. Each additional translation may add a node and a relationship to the language dependency graph, as well as fields in the database entries for a particular resource.

Figure 5:
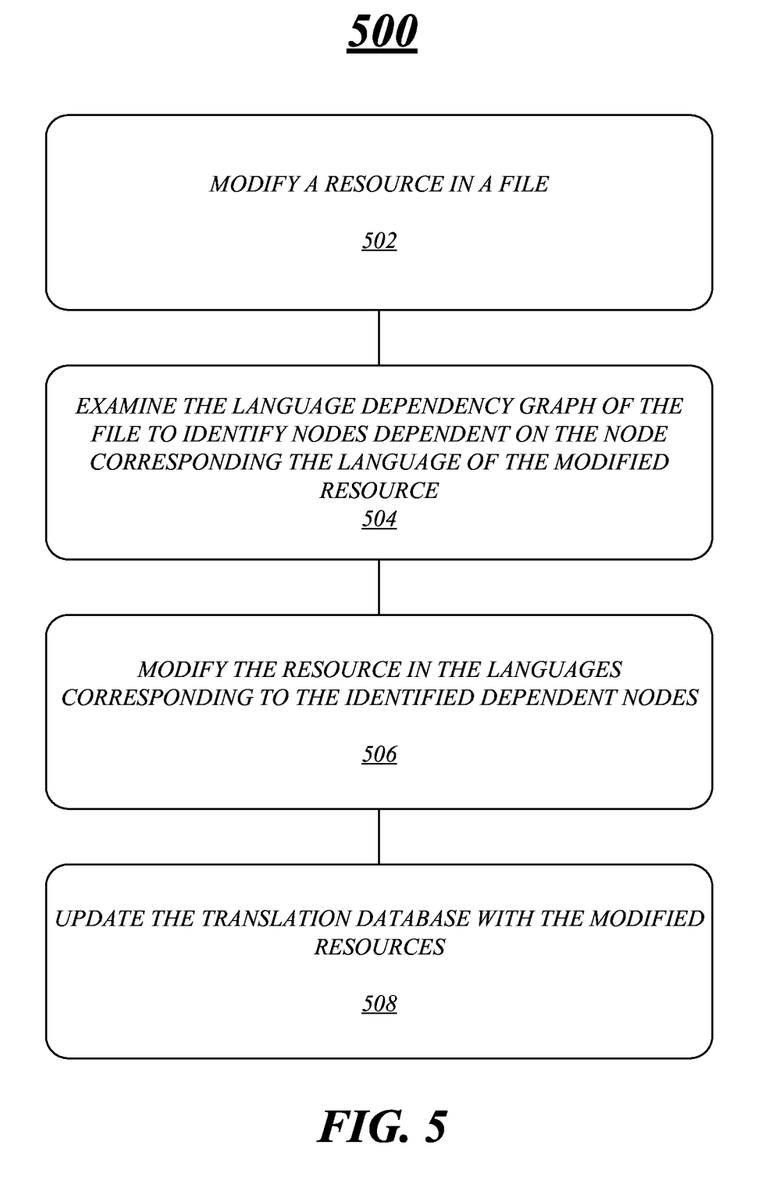
FIG. 5 illustrates an embodiment of a logic flow for using a language dependency graph in resource modification.

FIG. 5 illustrates one embodiment of a logic flow 500. The logic flow 500 may be representative of some or all of the operations executed by one or more embodiments described herein. Logic flow 500 may illustrate a technique for using a language dependency graph.

In the illustrated embodiment shown in FIG. 5, the logic flow 500 may modify a resource in a file at block 502. For example, the entity of origin of the resource files 140 may update a menu selection, or edit a help file.

The logic flow 500 may examine the language dependency graph for the file that contains the modified resource at block 504. For example, resource manager 110 may examine the language dependency graph to identify nodes that depend on the node that corresponds to the language of the modified resource. In the language dependency graph 300 illustrated in FIG. 3, for example, if a Spanish language resource is modified, then node 332 may be identified as being dependent on node 330, while the other nodes may be unaffected by the modification.

The logic flow 500 may modify the resource in the languages corresponding to the identified nodes at block 506. In the above example, the Catalan resource corresponding to the modified Spanish resource may be modified by a translator 120.

The logic flow 500 may update the translation database at block 508 to reflect the modified resources. For example, resource manager 110 may update the field in the data entry for the modified resource by replacing the previous version of the resource with the modified resource. In an embodiment, resource manager 110 may also update a revision number associated with the modified resource.

Figure 6:
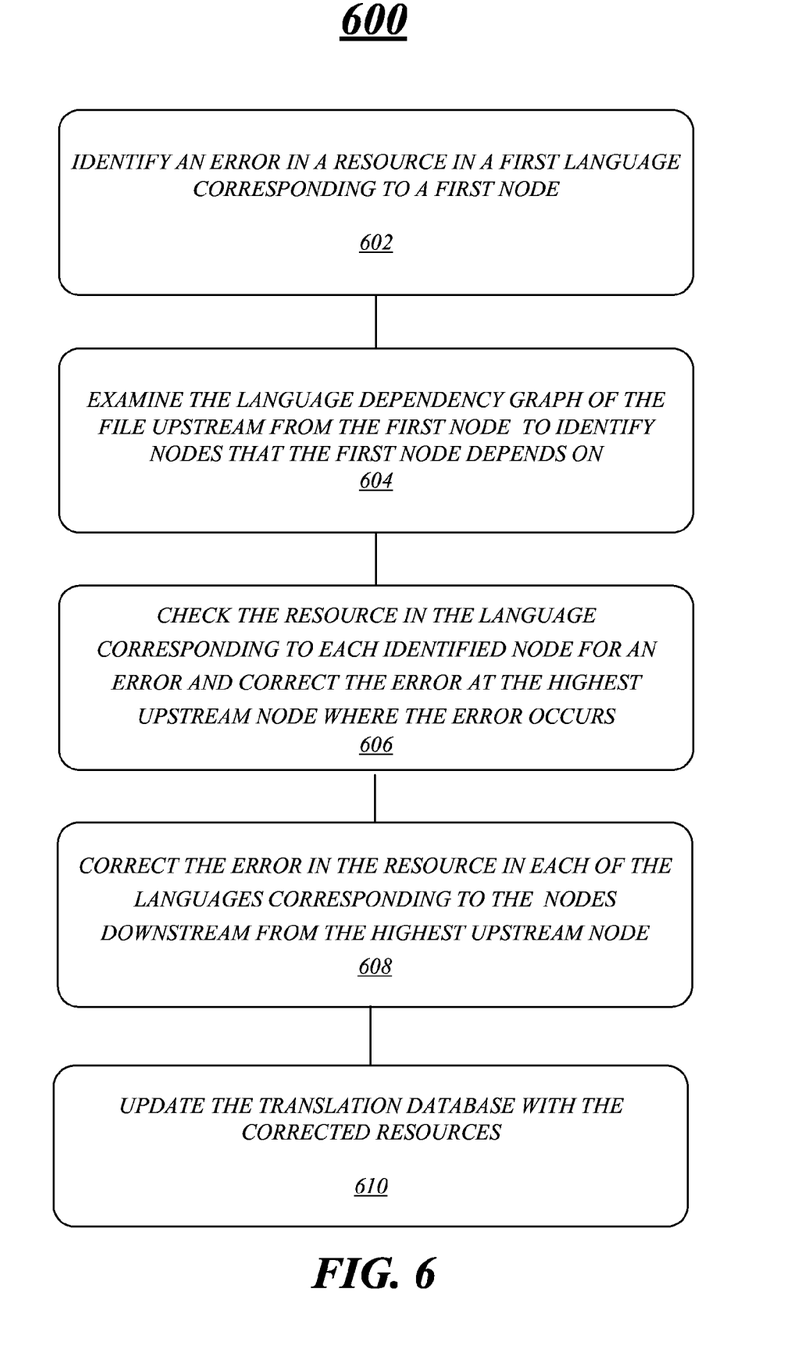
FIG. 6 illustrates an embodiment of a logic flow for using a language dependency graph for error detection and correction.

FIG. 6 illustrates one embodiment of a logic flow 600. The logic flow 600 may be representative of some or all of the operations executed by one or more embodiments described herein. Logic flow 600 may illustrate a technique for correcting errors using a language dependency graph.

In the illustrated embodiment shown in FIG. 6, the logic flow 600 may identify an error in a resource in a first language at block 602. For example, feedback from a client, user, developer, other localizer, reviewer, tester, product manager, international product engineer (IPE), and so forth may inform the entity of origin that a resource has been mistranslated. For the purposes of discussion of logic flow 600 "first language" refers to the language of the resource where the error is identified, and does not necessarily refer to the original language.

The logic flow 600 may examine the language dependency graph for the file that contains the erroneous resource in block 604. In particular, the language dependency graph may be examined in an "upstream" direction to identify the nodes and languages that the erroneous resource depends on. For example, in FIG. 3, if the error is identified in a French resource, corresponding to node 320, English node 310 is identified as an upstream node on which node 320 depends.

The logic flow 600 may check the resource in the languages corresponding to the identified nodes for an error at block 606. If there is more than one upstream node, then the resource may be checked in the language for each node until either the original node is reached, or until a correct version of the resource is located. For example, if the error is identified in Canadian French (node 322) in FIG. 3, then both the French resource (node 320) and the English resource (node 310) may be examined. If the French resource is incorrect but the English resource is correct, then node 320 is the highest upstream node where the error occurs. Logic flow 600 may repair the error in the highest upstream node also at block 606.

The logic flow 600 may correct the error in all of the languages downstream from the highest upstream node where the error occurred in block 608. If the error occurred originally in the French resource, then the resources corresponding to nodes 322, 324 and 326 may each need to be corrected.

The logic flow 600 may update the translation database at block 608 to reflect the modified resources. For example, resource manager 110 may update the data entry for the corrected resource by replacing the erroneous version of the resource with the corrected resource. In an embodiment, resource manager 110 may also update a revision number associated with the corrected resource.

Figure 7:
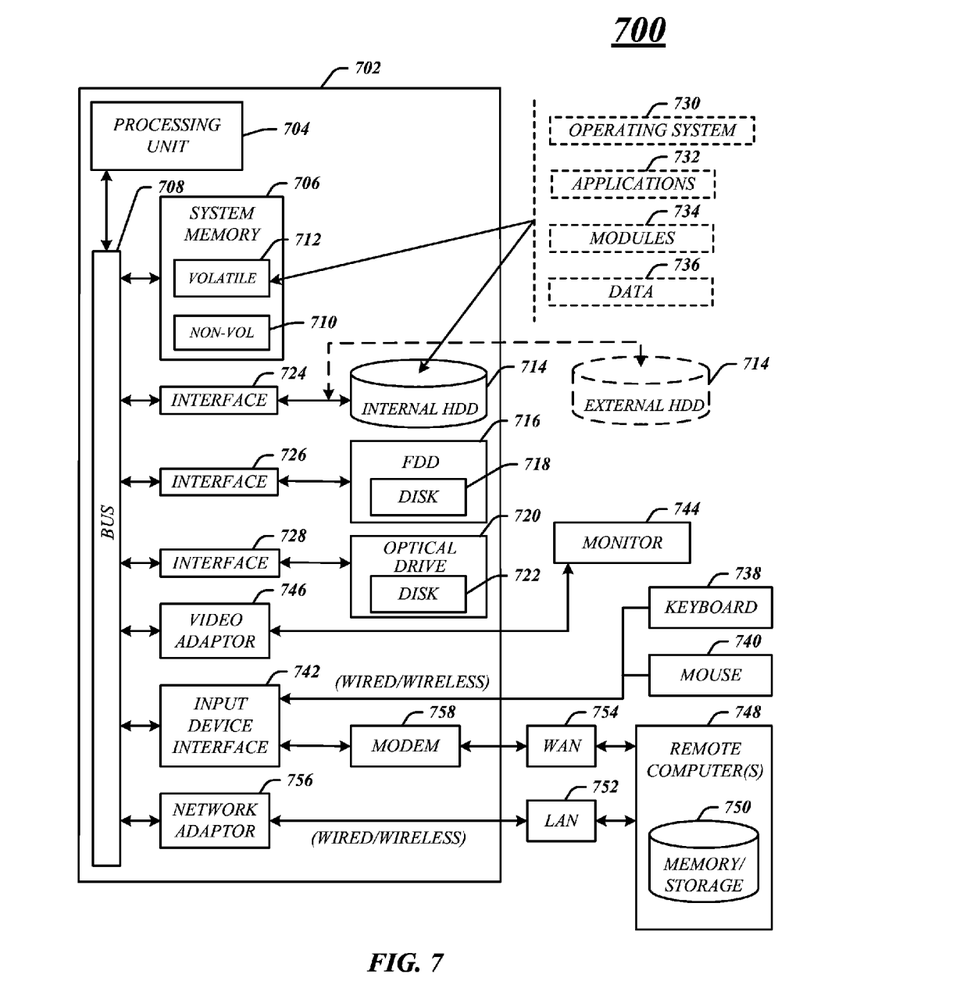
FIG. 7 illustrates an embodiment of a computing architecture.

FIG. 7 illustrates an embodiment of an exemplary computing architecture 700 suitable for implementing various embodiments as previously described. The computing architecture 700 includes various common computing elements, such as one or more processors, co-processors, memory units, chipsets, controllers, peripherals, interfaces, oscillators, timing devices, video cards, audio cards, multimedia input/output (I/O) components, and so forth. The embodiments, however, are not limited to implementation by the computing architecture 700.

As shown in FIG. 7, the computing architecture 700 comprises a processing unit 704, a system memory 706 and a system bus 708. The processing unit 704 can be any of various commercially available processors. Dual microprocessors and other multi-processor architectures may also be employed as the processing unit 704. The system bus 708 provides an interface for system components including, but not limited to, the system memory 706 to the processing unit 704. The system bus 708 can be any of several types of bus structure that may further interconnect to a memory bus (with or without a memory controller), a peripheral bus, and a local bus using any of a variety of commercially available bus architectures.

The system memory 706 may include various types of memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, or any other type of media suitable for storing information. In the illustrated embodiment shown in FIG. 7, the system memory 706 can include non-volatile memory 710 and/or volatile memory 712. A basic input/output system (BIOS) can be stored in the non-volatile memory 710.

The computer 702 may include various types of computer-readable storage media, including an internal hard disk drive (HDD) 714, a magnetic floppy disk drive (FDD) 716 to read from or write to a removable magnetic disk 718, and an optical disk drive 720 to read from or write to a removable optical disk 722 (e.g., a CD-ROM or DVD). The HDD 714, FDD 716 and optical disk drive 720 can be connected to the system bus 708 by a HDD interface 724, an FDD interface 726 and an optical drive interface 728, respectively. The HDD interface 724 for external drive implementations can include at least one or both of Universal Serial Bus (USB) and IEEE 1394 interface technologies. Computer-readable storage media may further include a storage area network (SAN) drive, and a solid state drive (SSD) (not shown).

The drives and associated computer-readable media provide volatile and/or nonvolatile storage of data, data structures, computer-executable instructions, and so forth. For example, a number of program modules can be stored in the drives and memory units 710, 712, including an operating system 730, one or more application programs 732, other program modules 734, and program data 736. The one or more application programs 732, other program modules 734, and program data 736 can include, for example, the resource manager 110 and the graph builder 130.

A user can enter commands and information into the computer 702 through one or more wire/wireless input devices, for example, a keyboard 738 and a pointing device, such as a mouse 740. Other input devices may include a microphone, an infra-red (IR) remote control, a joystick, a game pad, a stylus pen, touch screen, or the like. These and other input devices are often connected to the processing unit 704 through an input device interface 742 that is coupled to the system bus 708, but can be connected by other interfaces such as a parallel port, IEEE 1394 serial port, a game port, a USB port, an IR interface, and so forth.

A monitor 744 or other type of display device is also connected to the system bus 708 via an interface, such as a video adaptor 746. In addition to the monitor 744, a computer typically includes other peripheral output devices, such as speakers, printers, and so forth.

The computer 702 may operate in a networked environment using logical connections via wire and/or wireless communications to one or more remote computers, such as a remote computer 748. The remote computer 748 can be a workstation, a server computer, a router, a personal computer, portable computer, microprocessor-based entertainment appliance, a peer device or other common network node, and typically includes many or all of the elements described relative to the computer 702, although, for purposes of brevity, only a memory/storage device 750 is illustrated. The logical connections depicted include wire/wireless connectivity to a local area network (LAN) 752 and/or larger networks, for example, a wide area network (WAN) 754. Such LAN and WAN networking environments are commonplace in offices and companies, and facilitate enterprise-wide computer networks, such as intranets, all of which may connect to a global communications network, for example, the Internet.

When used in a LAN networking environment, the computer 702 is connected to the LAN 752 through a wire and/or wireless communication network interface or adaptor 756. The adaptor 756 can facilitate wire and/or wireless communications to the LAN 752, which may also include a wireless access point disposed thereon for communicating with the wireless functionality of the adaptor 756.

When used in a WAN networking environment, the computer 702 can include a modem 758, or is connected to a communications server on the WAN 754, or has other means for establishing communications over the WAN 754, such as by way of the Internet. The modem 758, which can be internal or external and a wire and/or wireless device, connects to the system bus 708 via the input device interface 742. In a networked environment, program modules depicted relative to the computer 702, or portions thereof, can be stored in the remote memory/storage device 750. It will be appreciated that the network connections shown are exemplary and other means of establishing a communications link between the computers can be used.

The computer 702 is operable to communicate with wire and wireless devices or entities using the IEEE 802 family of standards, such as wireless devices operatively disposed in wireless communication (e.g., IEEE 802.11 over-the-air modulation techniques) with, for example, a printer, scanner, desktop and/or portable computer, personal digital assistant (PDA), communications satellite, any piece of equipment or location associated with a wirelessly detectable tag (e.g., a kiosk, news stand, restroom), and telephone. This includes at least Wi-Fi (or Wireless Fidelity), WiMax, and Bluetooth™ wireless technologies. Thus, the communication can be a predefined structure as with a conventional network or simply an ad hoc communication between at least two devices. Wi-Fi networks use radio technologies called IEEE 802.11x (a, b, g, etc.) to provide secure, reliable, fast wireless connectivity. A Wi-Fi network can be used to connect computers to each other, to the Internet, and to wire networks (which use IEEE 802.3-related media and functions).

Figure 8:
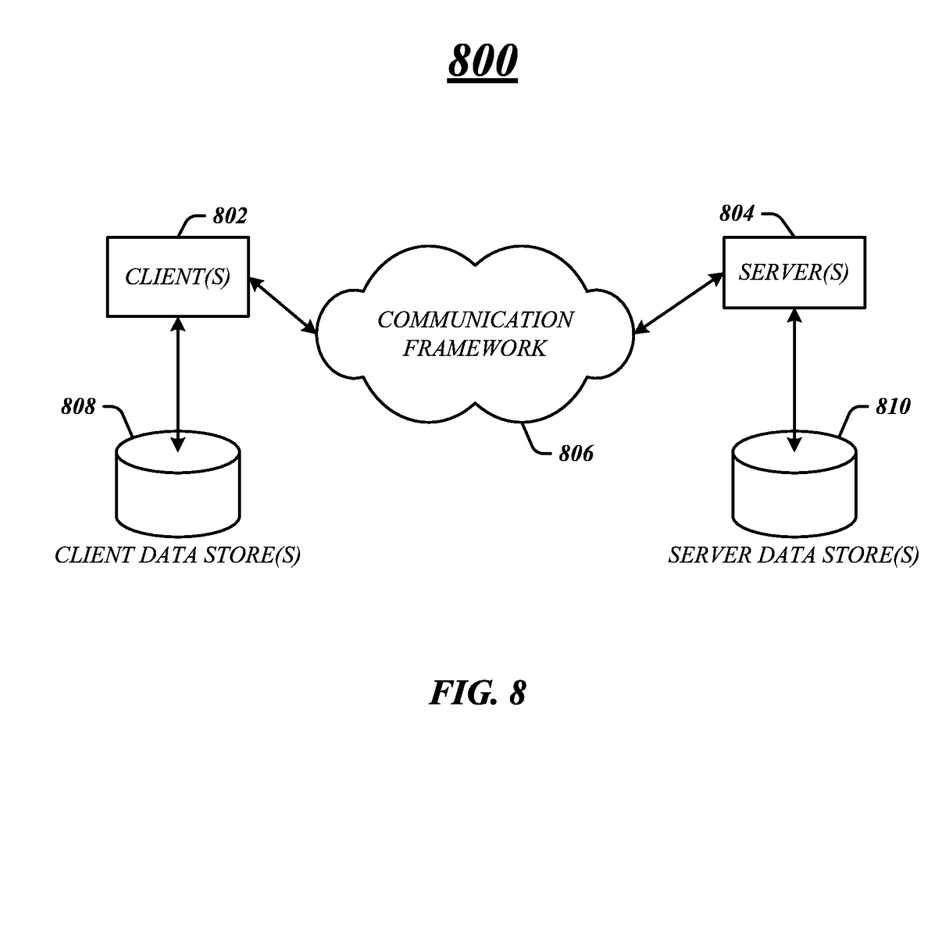
FIG. 8 illustrates an embodiment of a communications architecture.

FIG. 8 illustrates a block diagram of an exemplary communications architecture 800 suitable for implementing various embodiments as previously described. The communications architecture 800 includes various common communications elements, such as a transmitter, receiver, transceiver, radio, network interface, baseband processor, antenna, amplifiers, filters, and so forth. The embodiments, however, are not limited to implementation by the communications architecture 800.

As shown in FIG. 8, the communications architecture 800 comprises includes one or more clients 802 and servers 804. The clients 802 may implement a client system comprising resource manager 110 and graph builder 130. The servers 804 may implement a server system comprising translators 120 or resource files 140 and translation database 150. The clients 802 and the servers 804 are operatively connected to one or more respective client data stores 808 and server data stores 810 that can be employed to store information local to the respective clients 802 and servers 804, such as cookies and/or associated contextual information.

The clients 802 and the servers 804 may communicate information between each other using a communication framework 806. The communications framework 806 may implement any well-known communications techniques, such as techniques suitable for use with packet-switched networks (e.g., public networks such as the Internet, private networks such as an enterprise intranet, and so forth), circuit-switched networks (e.g., the public switched telephone network), or a combination of packet-switched networks and circuit-switched networks (with suitable gateways and translators). The clients 802 and the servers 804 may include various types of standard communication elements designed to be interoperable with the communications framework 806, such as one or more communications interfaces, network interfaces, network interface cards (NIC), radios, wireless transmitters/receivers (transceivers), wired and/or wireless communication media, physical connectors, and so forth. By way of example, and not limitation, communication media includes wired communications media and wireless communications media. Examples of wired communications media may include a wire, cable, metal leads, printed circuit boards (PCB), backplanes, switch fabrics, semiconductor material, twisted-pair wire, co-axial cable, fiber optics, a propagated signal, and so forth. Examples of wireless communications media may include acoustic, radio-frequency (RF) spectrum, infrared and other wireless media. One possible communication between a client 802 and a server 804 can be in the form of a data packet adapted to be transmitted between two or more computer processes. The data packet may include a cookie and/or associated contextual information, for example.

Various embodiments may be implemented using hardware elements, software elements, or a combination of both. Examples of hardware elements may include devices, logic devices, components, processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

Some embodiments may comprise an article of manufacture. An article of manufacture may comprise a storage medium to store logic. Examples of a storage medium may include one or more types of computer-readable storage media capable of storing electronic data, including volatile memory or non-volatile memory, removable or non-removable memory, erasable or non-erasable memory, writeable or re-writeable memory, and so forth. Examples of the logic may include various software elements, such as software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. In one embodiment, for example, an article of manufacture may store executable computer program instructions that, when executed by a computer, cause the computer to perform methods and/or operations in accordance with the described embodiments. The executable computer program instructions may include any suitable type of code, such as source code, compiled code, interpreted code, executable code, static code, dynamic code, and the like. The executable computer program instructions may be implemented according to a predefined computer language, manner or syntax, for instructing a computer to perform a certain function. The instructions may be implemented using any suitable high-level, low-level, object-oriented, visual, compiled and/or interpreted programming language.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It is emphasized that the Abstract of the Disclosure is provided to comply with 37 C.F.R. Section 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A method implemented by a computer comprising at least one processor, comprising:
    storing each resource from a file in a separate database entry, each entry comprising a first field comprising a first version of a resource and data indicating a first language and a dependency relationship to a source language indicating that the resource was translated from the source language to the first language;
    adding, to the database entry for the resource, a second field comprising a second version of the resource translated in a second language and data indicating a translating entity, the second language, and a dependency relationship indicating that the first language is a source language for the translation of the resource from the first language to the second language;
    generating a language dependency graph for the file, the graph comprising a first node for the first language and a second node for the second language coupled as a dependent to the first node according to the dependency relationship between the first and second languages;
    storing the language dependency graph for the file in the database entry associated with the file; and
    generating and storing a separate language dependency graph for a resource when the language dependency graph for the resource differs from the language dependency graph for the file.

2. The method of claim 1, further comprising:
    receiving a third version of the resource translated from the second language to a third language;
    adding, to the database entry for the resource, a third field comprising the third version of the resource and data indicating the translating entity, the third language, and a dependency relationship to the second language indicating that the second language is a source language for the translation of the resource from the second language to the third language; and
    updating the language dependency graph for the file with a third node for the third language coupled as a dependent to the second node.

3. The method of claim 2, wherein the third language is a derivative of the second language.

4. The method of claim 2, further comprising:
    modifying a resource in a file in one language;
    examining the language dependency graph of the file to identify nodes dependent on the node corresponding to the one language; and
    modifying the resource in the languages corresponding to the identified dependent nodes.

5. The method of claim 4, further comprising:
    modifying a plurality of resources in the file in the one language; and
    modifying the plurality of resources in the languages corresponding to the identified dependent nodes.

6. The method of claim 2, further comprising:
    identifying an error in a resource in a first language corresponding to a first node;
    examining the language dependency graph of the file upstream from the first node to identify nodes that the first node depends on;
    checking the resource in the language corresponding to each identified node for an error;
    correcting the error in the resource in the language at the highest upstream node where the error occurs; and
    correcting the error in the resource in each of the languages corresponding to nodes downstream from the highest upstream node.

7. The method of claim 6, wherein a field in a data entry for a resource further comprises data indicating an entity of origin of the resource, and the method further comprising:
    notifying the entity of origin corresponding to the language at the highest upstream node where the error occurs that the error originated at the entity; and
    notifying the entities of origin corresponding to each of the languages corresponding to nodes downstream from the highest upstream node that a correction will be needed.

8. The method of claim 1, further comprising:
    loading a resource from the file using database entry and the stored language dependency graph at run-time.

9. An article comprising a memory unit containing instructions that when executed enable a computing system to:
    store a resource for a file in a field in a database entry, the field comprising the resource and data indicating a language of the resource and a dependency relationship to a source language indicating that the resource was translated from the source language to the first language for the resource;
    store a second version of the resource in a different language in a second field in the database entry, the second field comprising the second version of the resource and data indicating a language of the resource and a dependency relationship indicating that the first language is a source language for the translation of the resource from the first language to the different language;
    generate a language dependency graph for the file according to the dependency relationship between the lan guages, the graph comprising a node for each language in the file, and a relationship between two nodes where the language of the first node is a source for a translation and the language of the second node is a target for the translation;

store the language dependency graph for the file in the database entry associated with the file; and generate and store a separate language dependency graph for a resource when the language dependency graph for the resource differs from the language dependency graph for the file.

10. The article of claim 9, further comprising instructions that when executed enable the computing system to:

receive a modified resource in a file in one language;

examine the language dependency graph of the file to identify nodes dependent on the node corresponding to the one language;

receive modifications to the resource in the languages corresponding to the identified dependent nodes; and update the database entry field for the modified resource to include the modified resource.

11. The article of claim 9, further comprising instructions that when executed enable the computing system to:

receive an identification of an error in a resource in a first language corresponding to a first node;

examine the language dependency graph of the file upstream from the first node to identify nodes that the first node depends on;

receive a correction of the error at the highest upstream node where the error occurs;

receive a correction of the error in the resource for each of the languages corresponding to nodes downstream from the highest upstream node; and update the database entry for the corrected resource to include the corrections resource.

12. The article of claim 11, wherein a field in a data entry for a resource further comprises data indicating an entity of origin of the resource, the article further comprising instructions that when executed enable the computing system to:

notify the entity of origin corresponding to the language at the highest upstream node where the error occurs that the error originated at the entity; and notify the entities of origin corresponding to each of the languages corresponding to nodes downstream from the highest upstream node that a correction will be needed.

13. The article of claim 9, further comprising instructions that when executed enable the computing system to:

load a resource from the file using the database entry for the resource and the stored language dependency graph at run-time.

14. An apparatus, comprising:

a logic device;

a resource manager operative on the logic device to generate a translation database comprising a section for a resource file, store a first version of each resource of the resource file in the translation database with data indicating a language of the resource and a dependency relationship to a source language indicating that the resource was translated from the source language to the language of the resource, and store a second version of a resource in a different language in the translation database with data indicating the language of the second version and a dependency relationship indicating that the language of the first version of the resource is a source language for the translation of the second version of the resource from the language of the first version of the resource to the language for the second version of the resource, store a language dependency graph in the translation database section for the file, and store a separate language dependency graph for a resource when the language dependency graph for the resource differs from the language dependency graph for the file; and a graph builder operative on the logic device to generate a language dependency graph for the file according to the dependency relationship between the languages, the graph comprising a node for each language in the section, and a relationship between two nodes where the language of the first node is a source for a translation and the language the second node is a target for the translation, and generate a separate language dependency graph for a resource when the language dependency graph for the resource differs from the language dependency graph for the file.

15. The apparatus of claim 14, the resource manager operative to receive a modification of a resource in a language, identify nodes downstream from a node corresponding to the language in the language dependency graph, and retrieve the resources related to the modified resource in the languages corresponding to the downstream nodes for modification.

16. The apparatus of claim 14, the resource manager operative to receive a notification of an error in a resource in a language, identify nodes upstream from a node corresponding to the language in the language dependency graph, and retrieve the resources related to the resource with the error in the languages corresponding to the upstream nodes for identification of the source of the error.

17. The apparatus of claim 16, the resource manager operative to store data indicating an entity of origin of the resource with each resource, notify the entity of origin corresponding to the language at the highest upstream node where the error occurs that the error originated at the entity.

* * * * *